(12) United States Patent
Santarelli et al.

(10) Patent No.: US 9,120,831 B2
(45) Date of Patent: Sep. 1, 2015

(54) PROCESS FOR THE PREPARATION OF BENZOHETERODIAZOLE COMPOUNDS DISUBSTITUTED WITH BENZODITHIOPHENE GROUPS

(71) Applicant: ENI S.p.A., Rome (IT)

(72) Inventors: Samuele Santarelli, Novara (IT); Gabriele Bianchi, L'Aquila (IT)

(73) Assignee: ENI S.p.A., Rome (IT)

( * ) Notice: Subject to any disclaimer, the term of this patent is extended or adjusted under 35 U.S.C. 154(b) by 0 days.

(21) Appl. No.: 14/250,673

(22) Filed: Apr. 11, 2014

(65) Prior Publication Data
US 2014/0309430 A1    Oct. 16, 2014

(30) Foreign Application Priority Data
Apr. 12, 2013    (IT) .............................. MI2013A0605

(51) Int. Cl.
*C07D 495/04*    (2006.01)
*C07D 519/00*    (2006.01)
*C07F 7/22*    (2006.01)

(52) U.S. Cl.
CPC ............ *C07F 7/2212* (2013.01); *C07D 495/04* (2013.01); *C07D 519/00* (2013.01)

(58) Field of Classification Search
None
See application file for complete search history.

(56) References Cited

FOREIGN PATENT DOCUMENTS

WO    WO 2011/120951 A1    10/2011
WO    WO 2013/021315 A1    2/2013

OTHER PUBLICATIONS

Nishide, et al., J. Org. Chem., 72:9141 (2007).*
Italian Search Report issued Sep. 13, 2013 in IT application MI2013 0605, filed on Apr. 12, 2013 ( with English Translation of Categories of Cited Documents).
Huaxing Zhou et al. "Donor-Acceptor Polymers Incorporating Alkylated Dithienylbenzothiadiazole for Bulk Heterojunction Solar Cells: Pronounced Effect for Positioning Alkyl Chains", Macromolecules Article, 2010, 10 pages.
Tianqi Cai et al. "Low bandgap polymers synthesized by $FeCl_3$ oxidative polymerization", Solar Energy Materials & Solar Cells 94, 2010, 7 pages.
Yosuke Nishide et al "Synthesis and Properties of a Series of Well-Defined and Polydisperse Benzo [1,2-b:4,3-b'] dithiophene Oligomers", JOC article, May 2007, 11 pages.
U.S. Appl. No. 14/250,687, filed Apr. 11, 2014, Alessi, et al.

* cited by examiner

*Primary Examiner* — Michael Barker
(74) *Attorney, Agent, or Firm* — Oblon, McClelland, Maier & Neustadt, L.L.P.

(57) ABSTRACT

Process for the preparation of a benzoheterodiazole compound disubstituted with benzodithiophene groups which comprises reacting at least one disubstituted benzoheterodiazole compound with at least one monostannylated benzodithiophene compound.

Said benzoheterodiazole compound disubstituted with benzodithiophene groups can be advantageously used in the construction of luminescent solar concentrators (LSCs). Furthermore, said benzoheterodiazole compound disubstituted with benzodithiophene groups can be advantageously used in the construction of photovoltaic devices (or solar devices) such as, for example, photovoltaic cells (or solar cells), photovoltaic modules (or solar modules), on both rigid and flexible supports. Furthermore, said benzoheterodiazole compound disubstituted with benzodithiophene groups can be advantageously used as precursor of monomeric units in the preparation of semiconductor polymers.

19 Claims, No Drawings

PROCESS FOR THE PREPARATION OF BENZOHETERODIAZOLE COMPOUNDS DISUBSTITUTED WITH BENZODITHIOPHENE GROUPS

The present invention relates to a process for the preparation of a benzoheterodiazole compound disubstituted with benzodithiophene groups.

More specifically, the present invention relates to a process for the preparation of a benzoheterodiazole compound disubstituted with benzodithiophene groups which comprises reacting at least one disubstituted benzoheterodiazole compound with at least one monostannylated benzodithiophene compound.

Said benzoheterodiazole compound disubstituted with benzodithiophene groups can be advantageously used in the construction of luminescent solar concentrators (LSCs). Furthermore, said benzoheterodiazole compound disubstituted with benzodithiophene groups can be advantageously used in the construction of photovoltaic devices (or solar devices) such as, for example, photovoltaic cells (or solar cells), photovoltaic modules (or solar modules), on both rigid and flexible supports. Furthermore, said benzoheterodiazole compound disubstituted with benzodithiophene groups can be advantageously used as precursor of monomeric units in the preparation of semiconductor polymers.

It is known that neither polymer nor silicon photovoltaic cells (or solar cells) which are currently the most widely-used on the market, are capable of efficiently exploiting all solar radiation. Their efficiency, in fact, is maximum only within a certain spectrum range which comprises a part of visible radiation and a part of infrared radiation.

Spectrum converter materials which capture solar radiation outside the optimal spectral range and convert it to effective radiation, can be used for enhancing the performance of photovoltaic cells (or solar cells). Luminescent solar concentrators (LSCs) can be produced with these materials, which allow a further increase in the production of current in photovoltaic cells (or solar cells).

Said luminescent solar concentrators (LSCs) generally consist of large sheets of material transparent to solar radiation, in which fluorescent substances are dispersed, which act as spectrum converters. Due to the effect of the optical phenomenon of total reflection, the radiation emitted by the fluorescent molecules is "guided" towards the thin edges of the sheet where it is concentrated on photovoltaic cells (or solar cells) positioned therein. In this way, large surfaces of low-cost materials (photoluminescent sheets) can be used for concentrating the light on small surfaces of high-cost materials [photovoltaic cells (or solar cells)].

It is known that compounds comprising a benzoheterodiazole group and at least a benzodithiophene group, such as, for example, 4,7-bis(7',8'-di(n-propyl)benzo[1',2'-b':4',3'-b"]dithien-5'-yl)benzo[c][1,2,5]thiadiazole, are fluorescent compounds which can be used as spectrum converter materials in luminescent solar concentrators. Materials of this type are described in Italian patent application MI2011A002405 in the name of the Applicant.

The above patent application also describes the synthesis of said compounds comprising a benzoheterodiazole group and at least a benzodithiophene group. Inter alia, the synthesis is described of 4,7-bis(7',8'-di(n-propyl)benzo[1',2'-b':4',3'-b"]dithien-5'-yl)benzo[c][1,2,5]thiadiazole, which is carried out according to the following Scheme 1:

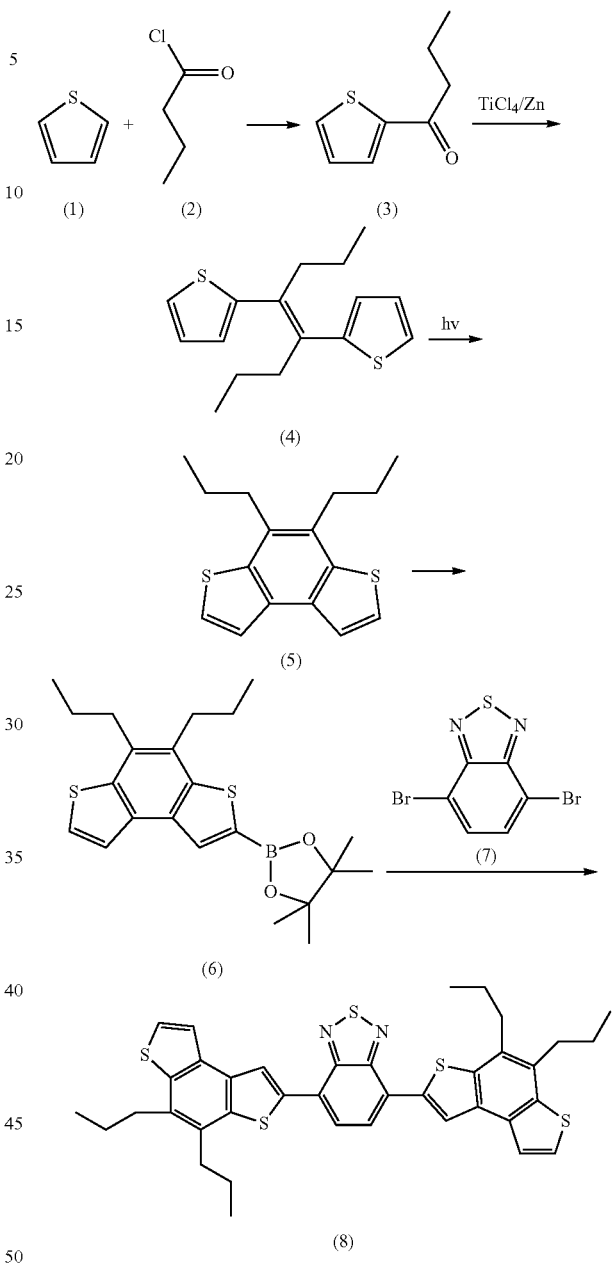

Scheme 1 wherein the thiophene having formula (1) is reacted with butyryl chloride having formula (2), operating according to what is reported by Sundby E. et al. in "*Arkivoc*" (2001), pages 76-84, obtaining 2'-thienyl-n-propylketone having formula (3) with a yield of 91%. The 2'-thienyl-n-propylketone having formula (3) is reacted, in the presence of anhydrous tetrahydrofuran (THF) with titanium tetrachloride (TiCl$_4$) and zinc (Zn) in powder form obtaining, after purification by means of chromatography on a silica gel column, (E)-4,5-bis (2'-thienyl)octene-4 having formula (4) with a yield of 83%. Said (E)-4,5-bis(2'-thienyl)octene-4 having formula (4) is subsequently introduced into a photoreactor, equipped with a 150 W medium-pressure mercury vapour lamp, together with toluene and iodine (I$_2$) obtaining, after purification by means of chromatography on a silica gel column, 7,8-di(n-propyl) benzo[1,2-b:4,3-b']dithiophene having formula (5) with a yield of 89%. Said 7,8-di(n-propyl)benzo[1,2-b:4,3-b']dithiophene having formula (5) is reacted, in an inert atmosphere, in the presence of anhydrous tetrahydrofuran (THF) with a 1.6 M solution of n-butyllithium in n-hexane and subsequently with 2-isopropoxy-4',4'',5',5''-tetramethyl-1',3',2'-dioxaborolane dissolved in anhydrous tetrahydrofuran (THF) obtaining, after purification by means of chromatography on a silica gel column, 2-(4',4'',5',5''-tetramethyl-1',3',2'-dioxoborolan-2'-yl)-7,8-di(n-propyl)benzo[1,2-b:4,3-b']dithiophene having formula (6) with a yield of 93%. Finally, a solution of 2-(4',4'',5',5''-tetramethyl-1',3',2'-dioxoborolan-2'-yl)-7,8-di(n-propyl)benzo[1,2-b:4,3-b']dithiophene having formula (6) in ethanol, is reacted in the presence of tetrakis (triphenylphosphine)palladium(0) [Pd(PPh$_3$)$_4$], 4,7-dibromobenzo[c][1,2,5]-thiadiazole having formula (7), degassed toluene, and a 2 M degassed aqueous solution of potassium carbonate (K$_2$CO$_3$), obtaining, after purification by means of chromatography on a silica gel column, 4,7-bis(7',8'-di(n-propyl)-benzo[1',2'-b':4',3'-b'']dithien-5'-yl)benzo[c][1,2,5]-thiadiazole having formula (8) with a yield of 15%. Further details relating to the synthesis of said 4,7-bis(7',8'-di(n-propyl)-benzo[1',2'-b':4',3'-b'']-dithien-5'-yl)benzo[c][1,2,5]-thiadiazole having formula (8) can be found in Italian patent application MI2011A002405 in the name of the Applicant reported above (in particular, in Example 3).

Although the above process allows compounds comprising a benzoheterodiazole group and at least a benzodithiophene group having a high purity (i.e. a purity higher than or equal to 95%) to be obtained, it can, however, have some disadvantages. In particular:
the yield of the final compound is low (i.e. yield lower than or equal to 15%);
there are numerous synthesis passages for obtaining the desired final compound with consequent higher process times and costs;
the purification of the products obtained at the end of each synthesis passage is carried out by means of chromatography on a silica gel column with consequent higher process times and costs;
necessity of a photochemical synthesis passage carried out in a photoreactor which is not easy to use on an industrial scale;
formations of high quantities of by-products with consequent problems due to their disposal which is often costly.

The Applicant has therefore considered the problem of finding a process for the preparation of a benzoheterodiazole compound disubstituted with benzodithiophene groups capable of overcoming the above drawbacks.

The Applicant has now found that the preparation of a benzoheterodiazole compound disubstituted with benzodithiophene groups can be carried out by means of a process which comprises reacting at least one disubstituted benzoheterodiazole compound with at least one monostannylated benzodithiophene compound.

There are numerous advantages obtained by operating according to the above process such as, for example:
high yield of the final compound (i.e. yield higher than or equal to 95%);
absence of purification steps by means of chromatography on a silica gel column of the products obtained at the end of each synthesis passage with consequent lower process times and costs;
absence of the photochemical synthesis passage carried out in a photoreactor and, consequently, easy use on an industrial scale;
formation of lower quantities of by-products with a consequent reduction in the disposal costs;
use of solvents having a low toxicity with consequent advantages from both an environmental point of view and also for the health of the operators, in addition to a reduction in the disposal costs.

Said benzoheterodiazole compound disubstituted with benzodithiophene groups can be advantageously used in the construction of luminescent solar concentrators (LSCS). Furthermore, said benzoheterodiazole compound disubstituted with benzodithiophene groups can be advantageously used in the construction of photovoltaic devices (or solar devices) such as, for example, photovoltaic cells (or solar cells), photovoltaic modules (or solar modules), on both rigid and flexible supports. Furthermore, said benzoheterodiazole compound disubstituted with benzodithiophene groups can be advantageously used as precursor of monomeric units in the preparation of semiconductor polymers.

An object of the present invention therefore relates to a process for the preparation of a benzoheterodiazole compound disubstituted with benzodithiophene groups having general formula (I):

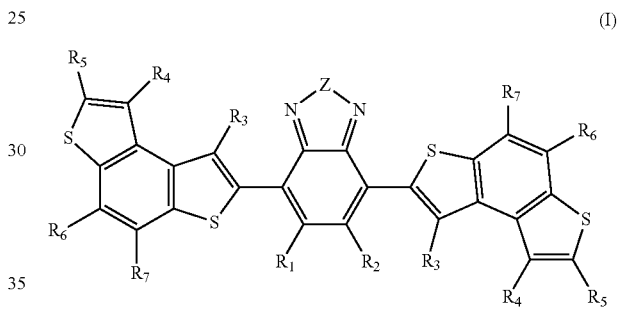

wherein:
Z represents a heteroatom selected from oxygen (O), sulfur (S), selenium (Se), preferably sulfur (S);
$R_1$, $R_2$, $R_3$, $R_4$, $R_5$, $R_6$ and $R_7$, equal to or different from each other, represent a hydrogen atom; or they are selected from linear or branched $C_1$-$C_{20}$, preferably $C_2$-$C_{10}$, alkyl groups, cycloalkyl groups optionally substituted, aryl groups optionally substituted, linear or branched $C_1$-$C_{20}$, preferably $C_2$-$C_{10}$, alkoxyl groups;
or $R_1$ and $R_2$ can be optionally bound to each other so as to form, together with the carbon atoms to which they are bound, a cycle or polycyclic system containing from 2 to 14 carbon atoms, preferably from 4 to 6 carbon atoms, saturated, unsaturated, or aromatic, optionally containing one or more heteroatoms such as, for example, oxygen, sulfur, nitrogen, silicon, phosphorous, selenium;
or $R_4$ and $R_5$ can be optionally bound to each other so as to form, together with the carbon atoms to which they are bound, a cycle or polycyclic system containing from 2 to 14 carbon atoms, preferably from 4 to 6 carbon atoms, saturated, unsaturated, or aromatic, optionally containing one or more heteroatoms such as, for example, oxygen, sulfur, nitrogen, silicon, phosphorous, selenium;
or $R_6$ and $R_7$ can be optionally bound to each other so as to form, together with the carbon atoms to which they are bound, a cycle or polycyclic system containing from 2 to 14 carbon atoms, preferably from 4 to 6 carbon atoms, saturated, unsaturated, or aromatic, optionally containing one or more heteroatoms such as, for example, oxygen, sulfur, nitrogen, silicon, phosphorous, selenium;

said process comprising reacting at least one disubstituted benzoheterodiazole compound having general formula (II):

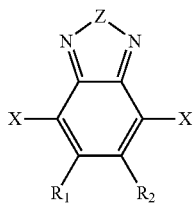

wherein X represents a halogen atom selected from chlorine, bromine, iodine, preferably bromine, Z, $R_1$ and $R_2$ have the same meanings described above; with at least one monostannylated benzodithiophene compound having general formula (III):

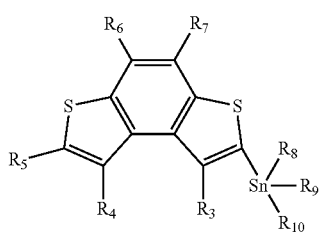

wherein $R_3$, $R_4$, $R_5$, $R_6$ and $R_7$, have the same meanings described above, and $R_8$, $R_9$ and $R_{10}$, equal to or different from each other, represent a hydrogen atom, or they are selected from linear or branched $C_1$-$C_{20}$, preferably $C_2$-$C_{10}$, alkyl groups, cycloalkyl groups optionally substituted.

For the aim of the present description and of the following claims, the definitions of the numerical ranges always comprise the extremes unless otherwise specified.

For the aim of the present description and of the following claims, the term "comprising" also includes the terms "which essentially consists of" or "which consists of".

The term "$C_1$-$C_{20}$ alkyl groups" refers to alkyl groups having from 1 to 20 carbon atoms, linear or branched. Specific examples of $C_1$-$C_{20}$ alkyl groups are: methyl, ethyl, n-propyl, iso-propyl, n-butyl, iso-butyl, t-butyl, pentyl, ethylhexyl, hexyl, heptyl, octyl, nonyl, decyl, dodecyl.

The term "cycloalkyl groups" refers to cycloalkyl groups having from 3 to 10 carbon atoms. Said cycloalkyl groups can be optionally substituted with one or more groups, equal to or different from each other, selected from: halogen atoms such as, for example, fluorine, chlorine, preferably fluorine; hydroxyl groups; $C_1$-$C_{20}$ alkyl groups; $C_1$-$C_{20}$ alkoxyl groups; cyano groups; amino groups; nitro groups. Specific examples of cycloalkyl groups are: cyclopropyl, 2,2-difluorocyclopropyl, cyclobutyl, cyclopentyl, cyclohexyl, methylcyclohexyl, methoxycyclohexyl, fluorocyclohexyl, phenylcyclohexyl.

The term "aryl groups" refers to aromatic carbocyclic groups. Said aryl groups can be optionally substituted with one or more groups, equal to or different from each other, selected from: halogen atoms such as, for example, fluorine, chlorine, preferably fluorine; hydroxyl groups; $C_1$-$C_{20}$ alkyl groups; $C_1$-$C_{20}$ alkoxyl groups, cyano groups; amino groups; nitro groups. Specific examples of aryl groups are: phenyl, methylphenyl, trimethylphenyl, methoxyphenyl, hydroxyphenyl, phenyloxyphenyl, fluorophenyl, pentafluorophenyl, chlorophenyl, nitrophenyl, dimethylamminophenyl, naphthyl, phenylnaphthyl, phenanthrene, anthracene.

The term "$C_1$-$C_{20}$ alkoxyl groups" refers to alkoxyl groups having from 1 to 20 carbon atoms, linear or branched. Specific examples of $C_1$-$C_{20}$ alkoxyl groups are: methoxyl, ethoxyl, n-propoxyl, iso-propoxyl, n-butoxyl, iso-butoxyl, t-butoxyl, pentoxyl, hexyloxyl, heptyloxyl, octyloxyl, nonyloxyl, decyloxyl, dodecyloxyl.

The term "cycle or polycyclic system" refers to a system containing one or more rings containing from 2 to 14 carbon atoms, optionally containing heteroatoms selected from nitrogen, oxygen, sulfur, silicon, selenium, phosphorous. Specific examples of a cycle or polycyclic system are: thieno[3,2-b]thiophene, thiadiazole, benzothiophene, quinoxaline, pyridine.

The above process can be carried out according to the following Scheme 2:

Scheme 2

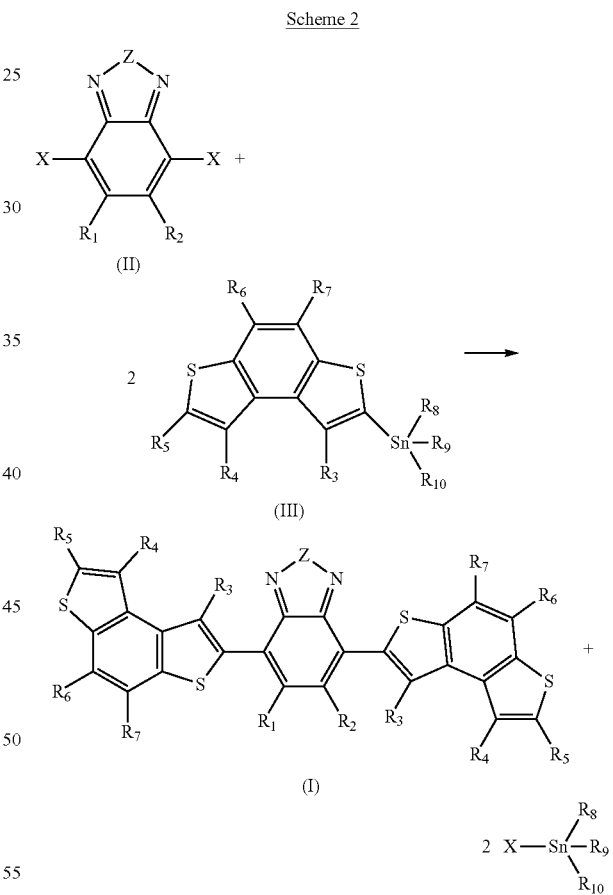

wherein Z, X, $R_1$, $R_2$, $R_3$, $R_4$, $R_5$, $R_6$, $R_7$, $R_8$, $R_9$ and $R_{10}$, have the same meanings described above.

According to a preferred embodiment of the present invention, said disubstituted benzoheterodiazole compound having general formula (II) and said monostannylated benzodithiophene compound having general formula (III) can be used in molar ratios ranging from 1:2 to 1:4, preferably ranging from 1:2 to 1:2.1.

According to a further preferred embodiment of the present invention, said process relates to the preparation of 4,7-bis(7', 8'-di(n-butyl)benzo[1',2'-b':4',3'-b"]dithien-5'-yl)-benzo[c][1,2,5]thiadiazole corresponding to a benzoheterodiazole compound disubstituted with benzodithiophene groups having general formula (I), wherein:

Z represents a sulfur atom;
$R_1$, $R_2$, $R_3$, $R_4$ and $R_5$, the same as each other, represent a hydrogen atom;
$R_6$ and $R_7$, the same as each other, represent a n-butyl group.

According to a preferred embodiment of the present invention, said process can be carried out in the presence of at least one catalyst containing palladium.

According to a preferred embodiment of the present invention, said catalyst containing palladium can be selected from: palladium compounds in oxidation state (0) or (II), preferably in oxidation state (II).

Specific examples of catalyst containing palladium which can be advantageously used for the aim of the present invention are:

dichloro[bis(triphenylphosphine)]palladium(II) [Pd(PPh$_3$)$_2$Cl$_2$];
[bis(triphenylphosphine)]palladium(II) diacetate[Pd(PPh$_3$)$_2$(ACO)$_2$];
tetrakis(triphenylphosphine)palladium(0) [Pd(PPh$_3$)$_4$];
bis(dibenzylideneacetone)palladium (0) [Pd(dba)$_2$ wherein dba=C$_6$H$_5$CH=CHCOCH=CHC$_6$H$_5$];
dichloro[bis(acetonitrile)]palladium(II) [Pd(CH$_3$CN)$_2$Cl$_2$];
benzylchloro[bis(triphenylphosphine)]palladium(II) [C$_6$H$_5$CH$_2$Pd(PPh$_3$)$_2$Cl];

or mixtures thereof.

Said catalyst containing palladium is preferably dichloro[bis(triphenylphosphine)]palladium(II) [Pd(PPh$_3$)$_2$Cl$_2$].

Said catalyst based on palladium can optionally be prepared in situ operating according to known techniques, by adding, to the reaction mixture, a palladium salt and a suitable ligand, dissolved in the reaction solvent selected from those reported hereunder [for example, non-anhydrous dimethylsulfoxide (DMSO), non-anhydrous N,N-dimethylformamide (DMF)]. Specific examples of palladium salts which can be advantageously used for the aim are: palladium chloride, palladium bromide, palladium nitrate, palladium acetate, palladium trifluoroacetate, palladium acetylacetonate. Specific examples of ligands which can be advantageously used for the aim are: trialkylphosphines or triarylphosphines, in particular, triphenylphosphine, o-tolylphosphine, m-tolylphosphine, p-tolylphosphine.

The complexes [bis(triphenylphosphine)]-palladio(II) diacetate[Pd(PPh$_3$)$_2$(AcO)$_2$] and dichloro[bis(triphenylphosphine)]palladium(II) [Pd(PPh$_3$)$_2$Cl$_2$], for example, can be formed in the reaction environment starting from commercial precursors such as triphenylphosphine and palladium(II) acetate or chloride, respectively. For this aim, the two reagents can be mixed, i.e. the disubstituted benzoheterodiazole compound having general formula (II) and the monostannylated benzodithiophene compound having general formula (III), the palladium salt and the ligand, in the reaction solvent selected from those reported hereunder [for example, non-anhydrous dimethylsulfoxide (DMSO), non-anhydrous N,N-dimethylformamide (DMF]: the reaction mixture obtained is then preferably put under a flow of nitrogen or argon. The mixture is heated to a temperature preferably ranging from 50° C. to 120° C. and the heating is continued until the reaction has been completed, preferably for a time ranging from 15 minutes to 2 hours.

If a preformed palladium complex is used, the two reagents can be mixed, i.e. the disubstituted benzoheterodiazole compound having general formula (II) and the monostannylated benzodithiophene compound having general formula (III), and the palladium-based catalyst, in the reaction solvent selected from those reported hereunder [for example, non-anhydrous dimethylsulfoxide (DMSO), non-anhydrous N,N-dimethylformamide (DMF)]: the reaction mixture obtained is then preferably put under a flow of nitrogen or argon. The mixture is heated to a temperature preferably ranging from 50° C. to 120° C. and the heating is continued until the reaction has been completed, preferably for a time ranging from 15 minutes to 2 hours.

In both cases, at the end of the process, the reaction mixture obtained is preferably immersed in a saturated aqueous solution of sodium chloride [NaCl$_{(sat.)}$] and ethyl acetate if non-anhydrous N,N-dimethylformamide (DMF) has been used, or in a saturated aqueous solution of sodium chloride [NaCl$_{(sat.)}$] and dichloromethane if non-anhydrous dimethylsulfoxide (DMSO) has been used. Two phases are obtained, which are separated: the desired product is recovered by evaporation from the organic phase, and can be purified by filtration and subsequent crystallization, whereas the aqueous phase is disposed of.

According to a preferred embodiment of the present invention, said disubstituted benzoheterodiazole compound having general formula (II) and said catalyst containing palladium can be used in molar ratios ranging from 100:0.1 to 100:3, preferably ranging from 100:0.4 to 100:2.5.

According to a preferred embodiment of the present invention, said disubstituted benzoheterodiazole compound having general formula (II) can be used at a molar concentration ranging from 0.01 M to 1 M, preferably ranging from 0.015 M to 0.06 M.

According to a preferred embodiment of the present invention, said process can be carried out in the presence of at least one non-anhydrous dipolar aprotic organic solvent.

For the aim of the present description and of the following claims, the term "non-anhydrous dipolar aprotic organic solvent" refers to an aprotic organic solvent containing a quantity of water not lower than or equal to 0.5% (v/v), preferably ranging from 1% (v/v) to 5% (v/v).

According to a preferred embodiment of the present invention, said non-anhydrous dipolar aprotic organic solvent can be selected, for example, from: non-anhydrous dimethylsulfoxide (DMSO), non-anhydrous N,N-dimethylformamide (DMF), non-anhydrous N,N-dimethylacetamide (DMAc), non-anhydrous N-methylpyrrolidone (NMP), or mixtures thereof. Said non-anhydrous dipolar aprotic organic solvent is preferably non-anhydrous dimethylsulfoxide (DMSO), non-anhydrous N,N-dimethylformamide (DMF).

According to a preferred embodiment of the present invention, said process can be carried out at a temperature ranging from 40° C. to 150° C., preferably ranging from 50° C. to 120° C.

According to a preferred embodiment of the present invention, said process can be carried out for a time ranging from 10 minutes to 10 hours, preferably ranging from 15 minutes to 2 hours.

The disubstituted benzoheterodiazole compound having general formula (II) can be obtained according to processes known in the art, for example, by halogenation of the corresponding benzoheterodiazole compounds. Further details relating to said processes can be found, for example, in international patent application WO 2007/081991, or in the article of Pilgram et al., "*Journal of Heterocyclic Chemistry*" (1970), Vol. 7, pages 629-633.

The monostannylated benzodithiophene compound having general formula (III) can be prepared according to the following Scheme 3:

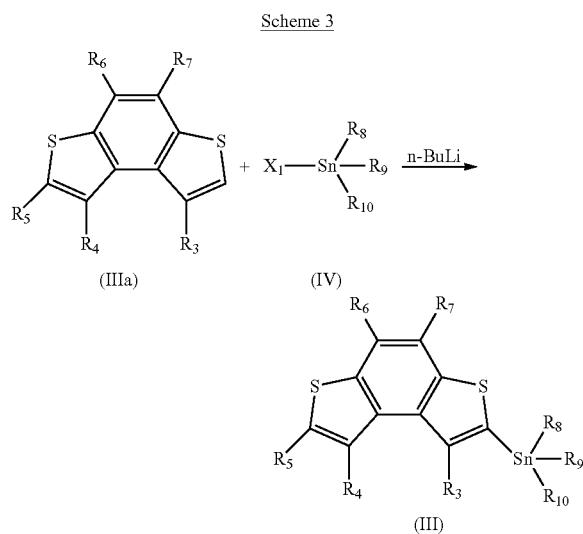

wherein $X_1$ represents a halogen atom selected from chlorine, bromine, iodine, preferably chlorine, $R_3$, $R_4$, $R_5$, $R_6$, $R_7$, $R_8$, $R_9$ e $R_{10}$, have the same meanings described above, by stannylation of a benzodithiophene compound having general formula (IIIa) with a trialkyl- or triaryl-tin halide having general formula (IV). Said stannylation reaction is carried out in the presence of n-butyllithium as described, for example, by Bundgaared et al., in "*Macromolecules*" (2006), pages 2823-2831. Further details are provided in the following examples.

The benzodithiophene compound having general formula (IIIa) can be prepared according to processes known in the art. It should be noted, however, that for the aim of the present invention, the benzodithiophene compound having general formula (IIIa) is preferably prepared by means of a process which comprises reacting at least one monohalogenated dithiophene compound having general formula (V):

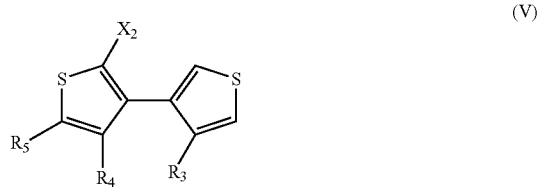

wherein $X_2$ represents a halogen atom selected from iodine, chlorine, bromine, preferably iodine, and $R_3$, $R_4$ and $R_5$ have the same meanings described above, with at least one internal alkine having general formula (VI):

wherein $R_6$ and $R_7$ have the same meanings described above; in the presence of at least one catalyst containing palladium and of at least one co-catalyst containing copper in oxidation state+1 having general formula (VII):

$CuX_3$ (VII)

wherein $X_3$ represents a halogen atom selected from iodine, chlorine, bromine, preferably iodine.

Further details relating to the above process can be found in Italian patent application MI2012A002052 in the name of the Applicant, whose content is incorporated herein as reference.

The present invention also relates to the monostannylated benzodithiophene compound having general formula (III) reported above.

Some illustrative and non-limiting examples are provided for a better understanding of the present invention and for its practical embodiment.

EXAMPLE 1

Synthesis of tri-n-butyl(7,8-dibutylbenzo[1,2-b:4,3-b']dithien-5-yl)stannane having formula (IIIc)

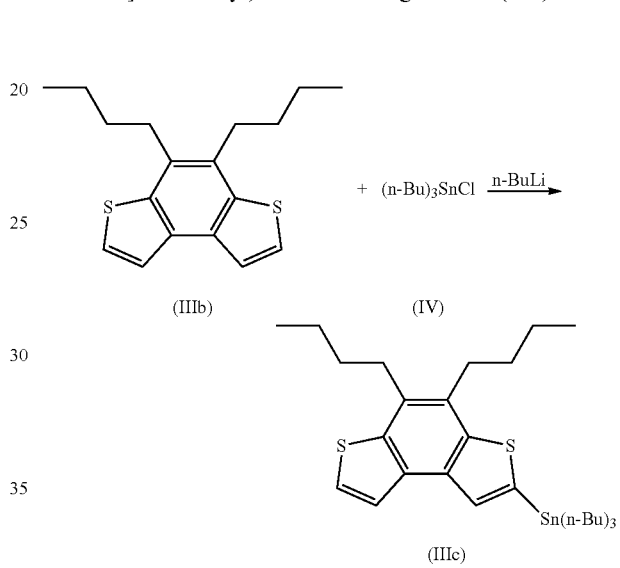

In a 250 ml three-necked glass flask equipped with magnetic stirring, an isobar drip funnel, two insufflators with taps and a perforable stopper, one insufflator was connected to the argon (Ar) line and the other to the vacuum pump. The insufflator connected to the argon (Ar) line was closed, that connected to the vacuum pump was opened and the vacuum pump was activated: the glass flask was contemporaneously heated to a temperature of 150° C., for 5 minutes, with a hot air gun, to desorb the humidity.

Said glass flask was cooled to room temperature (25° C.) and subjected to the so-called vacuum/argon (Ar) technique, i.e. the insufflator connected to the argon line (Ar) was opened for 30 seconds and a vacuum was then re-applied: said vacuum/argon (Ar) technique was repeated five times. 5.31 g (17.6 mmoles) of 7,8-di-n-butylbenzo[1,2-b:4,3-b'] dithiophene having formula (IIIb) (obtained as described in Example 1 of Italian patent application MI2012A002052) and 125 ml of freshly distilled tetrahydrofuran (THF) (Carlo Erba), were subsequently charged under a flow of argon (Ar). The whole was subjected to magnetic stirring and the glass flask was immersed in a cooling bath containing dry ice/acetone, at −78° C. 12 ml (19.2 mmoles) of n-butyllithium (n-BuLi) 1.6 M in n-hexane (Aldrich) were then introduced, in 30 minutes, by means of a drip funnel: the whole mixture was left, under vigorous stirring, at −78° C., for a further 30 minutes.

The cooling bath containing dry ice/acetone was subsequently substituted with a cooling bath containing water/ice and the temperature was brought to 0° C.: the whole mixture was left at 0° C., for 90 minutes. At the end, the glass flask was re-positioned in the cooling bath containing dry ice/acetone, at −78° C., and 5.8 ml (7.0 g, 21 mmoles) of tri-n-butyltin chloride having formula (IVb) (Aldrich) were introduced by means of another drip funnel previously anhydrified, in 20 minutes. The cooling bath containing dry ice/acetone was then removed and the whole mixture was left at room temperature (25° C.), for 19 hours. The advance degree of the reaction was then controlled, operating as follows: 0.1 ml of reaction mixture were removed from the glass flask and introduced into a test-tube containing 2 ml of ethyl ether (Aldrich) and 3 ml of a saturated aqueous solution of sodium bicarbonate [NaHCO$_{3(sat.)}$] (prepared with sodium bicarbonate of Aldrich) and the whole was subjected to stirring, obtaining a biphasic system comprising a prevalently ether phase and a prevalently aqueous phase. The prevalently ether phase was separated and subjected to thin layer chromatography (TLC) on silica gel using n-heptane (Carlo Erba) as eluent and an ultraviolet (UV) lamp as detector at 256 nm: said analysis indicated that tri-n-butyl(7,8-dibutylbenzo[1,2-b:4,3-b'] dithien-5-yl)stannane having formula (IIIc) had been formed with a yield equal to 100%.

The reaction mixture was then immersed in a separator funnel containing ethyl ether (Aldrich) and a saturated aqueous solution of sodium bicarbonate [NaHCO$_{3(sat.)}$] (prepared with sodium bicarbonate of Aldrich): the whole was subjected to stirring obtaining a biphasic system comprising a prevalently ether phase and a prevalently aqueous phase. The prevalently ether phase was separated and extracted three times with a saturated aqueous solution of sodium bicarbonate [NaHCO$_{3(sat.)}$] (prepared with sodium bicarbonate of Aldrich) to remove the tetrahydrofuran (THF) and the lithium chloride (LiCl) formed by the reaction: the aqueous phases obtained were joined and extracted twice with ethyl ether (Aldrich). The organic phases obtained at the end of the extractions were joined, dried on anhydrous sodium sulfate [Na$_2$SO$_{4(anhydrous)}$] (Aldrich) for minutes and subsequently filtered on cotton. The filtered solution was subjected to evaporation by means of a rotating evaporator obtaining 11.7 g of an oil containing: tri-n-butyltin chloride having formula (IV) in excess and 10.4 g of tri-n-butyl(7,8-dibutylbenzo[1, 2-b:4,3-b']dithien-5-yl)stannane having formula (IIIc) (100% yield).

EXAMPLE 2

Synthesis of 4,7-bis(7',8'-dibutylbenzo[1',2'-b':4',3'-b"]dithien-5'-yl)benzo[c]-[1,2,5]thiadiazole having formula (Ia)

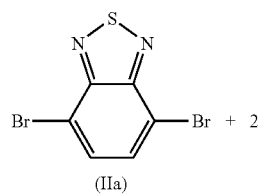

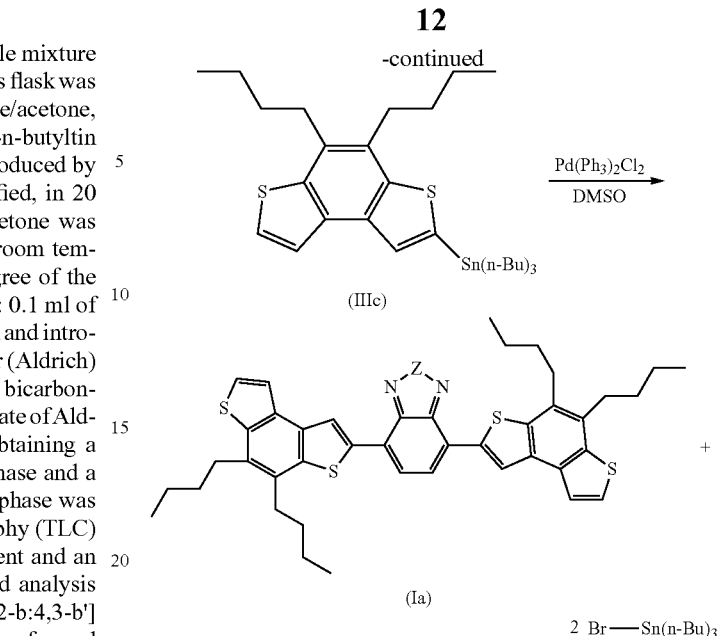

11.7 g of oil containing: tri-n-butyltin chloride having formula (IV) in excess and 10.4 g of tri-n-butyl(7,8-dibutyl-benzo[1,2-b:4,3-b']dithien-5-yl)-stannane having formula (IIIc) obtained in Example 1, 2.47 g (8.4 mmoles) of 4,7-dibromobenzo-[c][1,2,5]thiadiazole having formula (IIa) (Aldrich), 140 ml of non-anhydrous dimethylsulfoxide (DMSO) (Acros Organics) and 119 mg (0.17 mmoles) of dichloro[bis-(triphenylphosphine)]palladium(II) [Pd(PPh$_3$)$_2$Cl$_2$] (Aldrich), were charged into a 250 ml three-necked glass flask, equipped with magnetic stirring, an insufflator with a tap, a thermometer with a ground-glass cone and stopper: the whole mixture was subjected to stirring and put under a flow of argon (Ar).

The glass flask was then immersed in a preheated bath to bring the temperature of the reaction mixture to about 60° C. and left at this temperature for 1.5 hours. The advance degree of the reaction was then controlled, operating as follows: 0.1 ml of reaction mixture were removed from the glass flask and introduced into a test-tube containing 2 ml of dichloromethane (CH$_2$Cl$_2$) (Aldrich) and 3 ml of a saturated aqueous solution of sodium chloride [NaCl$_{(sat.)}$] (prepared with sodium chloride of Aldrich) and the whole mixture was subjected to stirring, obtaining a biphasic system comprising a prevalently organic phase and a prevalently aqueous phase. The prevalently organic phase was separated and subjected to thin layer chromatography (TLC) on silica gel using a mixture of n-heptane (Carlo Erba)/toluene (Aldrich) (10/2, v/v) as eluent and an ultraviolet (UV) lamp as detector at 365 nm: said analysis indicated that 4,7-bis(7',8'-dibutylbenzo[1',2'-b':4',3'-b"]dithien-5'-yl)benzo[c][1,2,5]thiadiazole having formula (Ia) had been formed with a yield equal to 95%.

The reaction mixture was then immersed in a separator funnel containing dichloromethane (CH$_2$Cl$_2$) (Aldrich) and a saturated aqueous solution of sodium chloride [NaCl$_{(sat.)}$] (prepared with sodium chloride of Aldrich): the whole mixture was subjected to stirring obtaining a biphasic system comprising a prevalently organic phase and a prevalently aqueous phase. The prevalently organic phase was separated and extracted three times with a saturated aqueous solution of sodium chloride [NaCl$_{(sat.)}$] (prepared with sodium chloride of Aldrich) to remove the dimethylsulfoxide (DMSO): the aqueous phases obtained were joined and extracted twice with dichloromethane ($CH_2Cl_2$) (Aldrich). The organic phases obtained at the end of the extractions were joined, dried on anhydrous calcium chloride [$CaCl_{2(anhydrous)}$] (Aldrich) for 45 minutes and filtered on a Buchner funnel, under vacuum. The solution obtained after filtration was subjected to evaporation by means of a rotating evaporator and the resulting oil was treated with an oil pump to eliminate the traces of solvent still present, obtaining a residue which was dissolved in the minimum possible volume of dichloromethane ($CH_2Cl_2$) (Aldrich), 10 g of silica ($SiO_2$) (Carlo Erba) were subsequently added and the mixture was then dried again with a rotating evaporator.

The powder obtained was placed on top of a silica panel ($SiO_2$) (Carlo Erba) to allow it to be filtered, initially with n-heptane (Aldrich), to remove all the impurities having a lower polarity, and subsequently with a mixture of n-heptane (Carlo Erba)/toluene (Aldrich) (10/2, v/v) to elute the 4,7-bis (7',8'-dibutylbenzo[1',2'-b':4',3'-b"]dithien-5'-yl)benzo[c]-[1,2,5]thiadiazole having formula (Ia), operating in a gradient of eluent with an increasing polarity until pure toluene to complete the filtration. The filtrate obtained was evaporated to dryness using a rotating evaporator, obtaining a solid which was dissolved in the minimum possible volume of dichloromethane ($CH_2Cl_2$) (Aldrich) and brought to boiling point, under a flow of nitrogen ($N_2$), the volume was then doubled with t-butylmethylether (Aldrich), brought again to boiling point and left to boil until the volume was halved. The whole mixture was left to cool to room temperature (25° C.) and was then cooled to 0° C. with a water and ice bath, subjected to filtration and washed with t-butylmethylether (Aldrich) at 0° C., obtaining 5.9 g of dark brick-red crystals of pure 4,7-bis (7',8'-dibutylbenzo[1',2'-b':4',3'-b"]dithien-5'-yl)benzo[c]-[1,2,5]thiadiazole having formula (Ia) (yield 95%).

The invention claimed is:

1. A process for preparing a benzoheterodiazole compound disubstituted with benzodithiophene groups having formula (I):

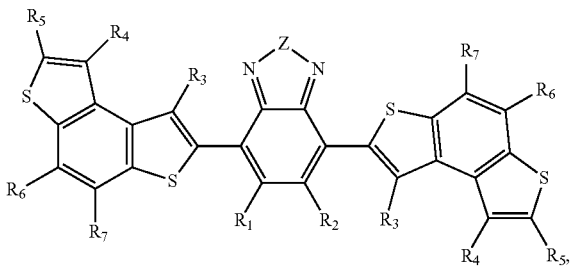

(I)

wherein:
Z represents a heteroatom selected from the group consisting of oxygen (O), sulfur (S), selenium (Se), and tellurium (Te); and
$R_1$, $R_2$, $R_3$, $R_4$, $R_5$, $R_6$ and $R_7$ independently represent a hydrogen atom, or they are selected from the group consisting of a linear or branched $C_1$-$C_{20}$ alkyl group, a cycloalkyl group optionally substituted, an aryl group optionally substituted, and a linear or branched $C_1$-$C_{20}$ alkoxyl group,
wherein $R_1$ and $R_2$ are optionally bound to each other so as to form, together with the carbon atoms to which they are bound, a cycle or polycyclic system comprising from 2 to 14 carbon atoms, saturated, unsaturated, or aromatic, optionally comprising one or more of oxygen, sulfur, nitrogen, silicon, phosphorous, and selenium,
wherein $R_4$ and $R_5$ are optionally bound to each other so as to form, together with the carbon atoms to which they are bound, a cycle or polycyclic system comprising from 2 to 14 carbon atoms, saturated, unsaturated, or aromatic, optionally comprising one or more of oxygen, sulfur, nitrogen, silicon, phosphorous, and selenium, and
wherein $R_6$ and $R_7$ are optionally bound to each other so as to form, together with the carbon atoms to which they are bound, a cycle or polycyclic system comprising from 2 to 14 carbon atoms, saturated, unsaturated, or aromatic, optionally comprising one or more of oxygen, sulfur, nitrogen, silicon, phosphorous, and selenium, said process comprising reacting at least one disubstituted benzoheterodiazole compound of formula (II):

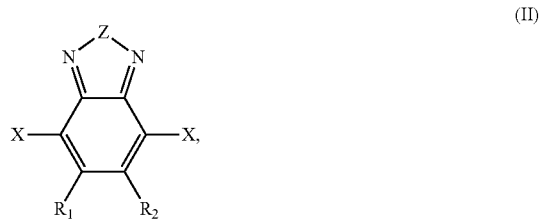

(II)

with at least one monostannylated benzodithiophene compound of formula (III):

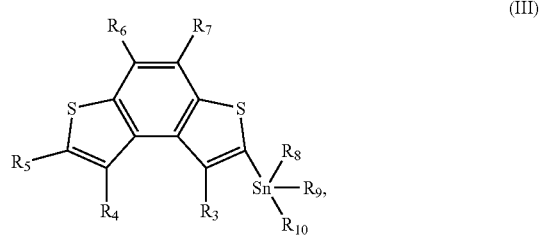

(III)

wherein:
X represents a halogen atom selected from the group consisting of chlorine, bromine, and iodine,
Z, $R_1$ and $R_2$ in formula (II) have the same definition as they do in formula (I);
$R_3$, $R_4$, $R_5$, $R_6$ and $R_7$ in formula (III) have the same definition as they do in formula (I); and
$R_8$, $R_9$ and $R_{10}$ independently represent a hydrogen atom, or they are selected from the group consisting of a linear or branched $C_1$-$C_{20}$ alkyl group, and a cycloalkyl group optionally substituted.

2. The process according to claim 1, wherein said disubstituted benzoheterodiazole compound having general formula (II) and said monostannylated benzodithiophene compound having general formula (III) are reacted in molar ratios ranging from 1:2 to 1:4.

3. The process according to claim 1, wherein said process forms 4,7-bis(7',8'-di-n-butylbenzo[1',2'-b':4',3'-b"]dithien-5'-yl)-benzo[c][1,2,5]thiadiazole from a corresponding benzoheterodiazole compound of formula (I), wherein:

Z represents a sulfur atom;

$R_1$, $R_2$, $R_3$, $R_4$ and $R_5$ independently represent a hydrogen atom; and $R_6$ and $R_7$ independently represent an n-butyl group.

4. The process according to claim 1, wherein said process occurs in the presence of at least one catalyst comprising palladium.

5. The process according to claim 4, wherein said catalyst comprises palladium in an oxidation state of (0) or (II).

6. The process according to claim 4, wherein said catalyst is dichloro-[bis(triphenylphosphine)]palladium(II) [Pd(PPh$_3$)$_2$Cl$_2$].

7. The process according to claim 4, wherein said disubstituted benzoheterodiazole compound having general formula (II) and said catalyst are present in molar ratios ranging from 100:0.1 to 100:3.

8. The process according to claim 1, wherein said disubstituted benzoheterodiazole compound having general formula (II) is present in a molar concentration ranging from 0.01 M to 1 M.

9. The process according to claim 1, wherein said process occurs in the presence of at least one non-anhydrous dipolar aprotic organic solvent.

10. The process according to claim 9, wherein said non-anhydrous dipolar aprotic organic solvent is selected from the group consisting of non-anhydrous dimethylsulfoxide (DMSO), non-anhydrous N,N-dimethylformamide (DMF), non-anhydrous N,N-dimethylacetamide (DMAc), non-anhydrous N-methylpyrrolidone (NMP), and mixtures thereof.

11. The process according to claim 1, wherein said process occurs at a temperature ranging from 40° C. to 150° C.

12. The process according to claim 1, wherein said process occurs over a time ranging from 10 minutes to 10 hours.

13. The process according to claim 1, wherein:

said disubstituted benzoheterodiazole compound having general formula (II) and said monostannylated benzodithiophene compound having general formula (III) are reacted in molar ratios ranging from 1:2 to 1:4;

said process occurs in the presence of at least one catalyst comprising palladium in an oxidation state of (0) or (II);

said disubstituted benzoheterodiazole compound having general formula (II) and said catalyst are present in molar ratios ranging from 100:0.1 to 100:3;

said process occurs in the presence of at least one non-anhydrous dipolar aprotic organic solvent;

said process occurs at a temperature ranging from 40° C. to 150° C.; and said process occurs over a time ranging from 10 minutes to 10 hours.

14. The process according to claim 13, wherein said process forms 4,7-bis(7',8'-di-n-butylbenzo[1',2'-b':4',3'-b'']dithien-5'-yl)-benzo[c][1,2,5]thiadiazole from a corresponding benzoheterodiazole compound of formula (I), wherein:

Z represents a sulfur atom;

$R_1$, $R_2$, $R_3$, $R_4$ and $R_5$ independently represent a hydrogen atom; and $R_6$ and $R_7$ independently represent an n-butyl group.

15. The process according to claim 14, wherein said catalyst is dichloro-[bis(triphenylphosphine)]palladium(II) [Pd(PPh$_3$)$_2$Cl$_2$].

16. The process according to claim 1, wherein the yield of said benzoheterodiazole compound disubstituted with benzodithiophene groups having formula (I) is 95% or greater.

17. The process according to claim 3, wherein the yield of said benzoheterodiazole compound disubstituted with benzodithiophene groups having formula (I) is 95% or greater.

18. The process according to claim 13, wherein the yield of said benzoheterodiazole compound disubstituted with benzodithiophene groups having formula (I) is 95% or greater.

19. The process according to claim 15, wherein the yield of said benzoheterodiazole compound disubstituted with benzodithiophene groups having formula (I) is 95% or greater.

* * * * *